US007592608B2

(12) United States Patent
Shakespeare et al.

(10) Patent No.: US 7,592,608 B2
(45) Date of Patent: Sep. 22, 2009

(54) APPARATUS AND METHOD FOR MEASURING AND/OR CONTROLLING ULTRAVIOLET-ACTIVATED MATERIALS IN A PAPER-MAKING PROCESS

(75) Inventors: Tarja T. Shakespeare, Savo (FI); John F. Shakespeare, Savo (FI)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/017,497

(22) Filed: Jan. 22, 2008

(65) Prior Publication Data

US 2009/0184257 A1 Jul. 23, 2009

(51) Int. Cl.
*G01N 21/64* (2006.01)

(52) U.S. Cl. .................................................. 250/461.1

(58) Field of Classification Search ............... 250/461.1
See application file for complete search history.

(56) References Cited

U.S. PATENT DOCUMENTS 4,006,358 A 2/1977 Howarth
4,288,691 A 9/1981 Horton
4,376,946 A 3/1983 Kaminow et al.
4,439,038 A 3/1984 Mactaggart
4,565,444 A 1/1986 Mactaggart
4,592,043 A 5/1986 Williams
4,634,928 A 1/1987 Figueroa et al.
4,699,510 A 10/1987 Alguard
4,786,817 A 11/1988 Boissevain et al.
4,807,630 A 2/1989 Malinouskas
4,856,014 A 8/1989 Figueroa et al.
4,883,963 A 11/1989 Kemeny et al.

(Continued)

FOREIGN PATENT DOCUMENTS

DE 3148076 A1 6/1983

(Continued)

OTHER PUBLICATIONS

Robert L. Feller, "Comments on the Measurement of "Yellowness" in Pulp and Paper," The Book and Paper Group Annual, vol. Six 1987, The American Institute for Conservation, May 1987, 9 pages.

(Continued)

*Primary Examiner*—David P Porta
*Assistant Examiner*—Mindy Vu
(74) *Attorney, Agent, or Firm*—Carter Munck, LLP

(57) ABSTRACT

A method includes illuminating a mixture of materials in a wet-end of a paper process, where the mixture includes an ultraviolet-activated material. The method also includes measuring light from the mixture and determining a property of the ultraviolet-activated material based on the measured light. The method may further include adjusting an operation in the wet-end of the paper process based on the determined property of the ultraviolet-activated material. The determined property could include a quantity of fluorescent material in recycled material used to form stock for a paper machine and/or a quantity of fluorescent material in stock provided to a headbox in the paper process. Adjusting the operation in the wet-end could include adjusting an amount of one or more materials used to form stock provided to the headbox, such as a fluorescent whitening agent, fixative, fluorescent fiber, fluorescent pigment, fluorescent particle, fluorescent highlight, fluorescent planchette, or fluorescent quencher.

21 Claims, 6 Drawing Sheets

200
INTERFACE
212
DETECTOR CONTROLLER
210
DETECTOR 206
208
204
202

U.S. PATENT DOCUMENTS

| | | | |
|---|---|---|---|
| 4,928,013 | A | 5/1990 | Howarth et al. |
| 5,015,099 | A | 5/1991 | Nagai et al. |
| 5,047,652 | A | 9/1991 | Lisnyansky et al. |
| 5,122,974 | A | 6/1992 | Chance |
| 5,137,364 | A | 8/1992 | McCarthy |
| 5,220,172 | A | 6/1993 | Berthold et al. |
| 5,235,192 | A | 8/1993 | Chase et al. |
| 5,313,187 | A | 5/1994 | Choi et al. |
| 5,338,361 | A | 8/1994 | Anderson et al. |
| 5,374,555 | A | 12/1994 | Pokora et al. |
| 5,400,258 | A | 3/1995 | He |
| 5,642,189 | A | 6/1997 | Alguard |
| 5,642,192 | A | 6/1997 | Gordon et al. |
| 5,774,213 | A | 6/1998 | Trebino et al. |
| 5,793,486 | A | 8/1998 | Gordon et al. |
| 5,795,394 | A | 8/1998 | Belotserkovsky et al. |
| 5,821,536 | A | 10/1998 | Pettit |
| 5,933,243 | A | 8/1999 | Hagen |
| 5,963,333 | A | 10/1999 | Walowit et al. |
| 5,992,318 | A | 11/1999 | DiBello et al. |
| 6,058,201 | A | 5/2000 | Sikes et al. |
| 6,074,483 | A | 6/2000 | Belotserkovsky et al. |
| 6,263,291 | B1 | 7/2001 | Shakespeare et al. |
| 6,272,440 | B1 | 8/2001 | Shakespeare et al. |
| 6,466,839 | B1 | 10/2002 | Heaven et al. |
| 6,499,402 | B1 | 12/2002 | Sikes et al. |
| 6,556,305 | B1 | 4/2003 | Aziz et al. |
| 6,584,435 | B2 | 6/2003 | Mestha et al. |
| 6,603,551 | B2 | 8/2003 | Mestha et al. |
| 6,724,473 | B2 | 4/2004 | Leong et al. |
| 6,743,337 | B1 | 6/2004 | Ischdonat |
| 6,760,103 | B2 | 7/2004 | Shakespeare et al. |
| 6,763,322 | B2 | 7/2004 | Potyrailo et al. |
| 6,805,899 | B2 | 10/2004 | MacHattie et al. |
| 6,856,436 | B2 | 2/2005 | Brukilacchio et al. |
| 6,949,734 | B2 | 9/2005 | Neff et al. |
| 7,199,884 | B2 | 4/2007 | Jasinski et al. |
| 7,291,856 | B2 | 11/2007 | Haran et al. |
| 2003/0058441 | A1 | 3/2003 | Shakespeare et al. |
| 2004/0119781 | A1 | 6/2004 | Szumla |
| 2004/0212804 | A1 | 10/2004 | Neff et al. |
| 2004/0260520 | A1 | 12/2004 | Braendle et al. |
| 2005/0065400 | A1 | 3/2005 | Banik et al. |
| 2005/0156116 | A1* | 7/2005 | Schuett et al. .............. 250/372 |
| 2006/0132796 | A1 | 6/2006 | Haran |
| 2006/0237156 | A1* | 10/2006 | Shakespeare et al. ....... 162/198 |
| 2006/0243931 | A1 | 11/2006 | Haran et al. |
| 2007/0139735 | A1 | 6/2007 | Shakespeare et al. |
| 2007/0144388 | A1 | 6/2007 | Shakespeare et al. |
| 2007/0153277 | A1 | 7/2007 | Shakespeare et al. |
| 2007/0153278 | A1 | 7/2007 | Shakespeare et al. |

FOREIGN PATENT DOCUMENTS

| | | | |
|---|---|---|---|
| DE | 19515499 | A1 | 10/1996 |
| EP | 0 319 158 | A1 | 6/1989 |
| EP | 1437222 | A1 | 7/2004 |
| EP | 1457335 | A1 | 9/2004 |
| EP | 1 491 877 | A1 | 12/2004 |
| WO | WO 84/00181 | A1 | 1/1984 |
| WO | WO 03/037111 | A1 | 5/2003 |

OTHER PUBLICATIONS

M. K. Ramasubramanian et al., "Optical Sensor for Noncontact Measurement of Lignin Content in High-Speed Moving Paper Surfaces," IEEE Sensors Journal, vol. 5, No. 5, Oct. 2005, pp. 1132-1139.

C. I. Thomson et al., "Excitation Energy Transfer in Lignin: Fluorescence of Kraft Residual Lignin," 2004, 1 page.

S. Katuscak et al., "The Effect of Paper Degradation on Uncertainty of Determination of Initial Lignin Content," 2006, 3, pp. 69-72.

D.P. Koullas et al., "Fluorescence Spectroscopy for the Characterisation of Lignocellulosics-An Overview of the Recent Research," National Technical University of Athens, Bioresource Technology Unit, 2004, 57 pages.

Bo Albinsson et al., "The Origin of Lignin Fluorescence," Journal of Molecular Structure 508 (1999), pp. 19-27.

Tarja Shakespeare et al., "Problems in Colour Measurement of Fluorescent Paper Grades", Anlytica Chimica Acta 380 (1999), pp. 227-242.

Tarja Shakespeare et al., "Advanced Colour Control Through Reflectance Optimization", Proceedings 2nd EcoPaperTech Conference, Helsinki Finland, Jun. 1998, pp. 183-194.

Custom Optics, "Filter, Color Sensor", 2008 JDS Uniphase Corporation, 6 pages.

Stokman et al., "Color Measurement by Imaging Spectrometry", Computer Vision & Image Understanding, San Diego, CA, US, vol. 79, No. 2, Aug. 2000, pp. 236-249.

Wandell, "Color Management and Discrimination", Journal of the Optical Society of America, USA, vol. 2, No. 1, Jan. 1985, pp. 62-71.

Tarja T. Shakespeare et al., "Apparatus and Method for Measuring and/or Controlling Paper Pulp Properties", U.S. Appl. No. 12/017,092, filed Jan. 21, 2008.

Tarja T. Shakespeare et al., "Apparatus and Method for Camera-Based Color Measurements", U.S. Appl. No. 12/017,469, filed Jan. 22, 2008.

* cited by examiner

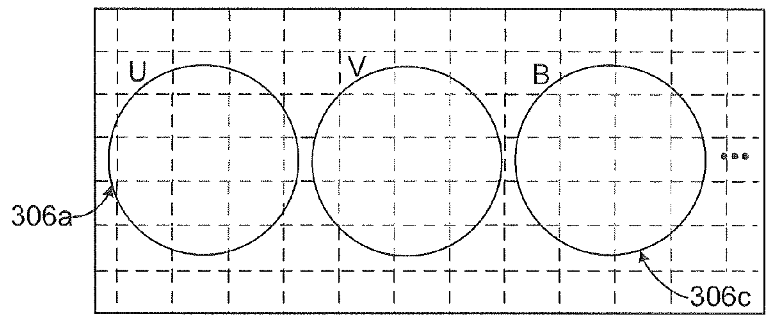
FIGURE 3C
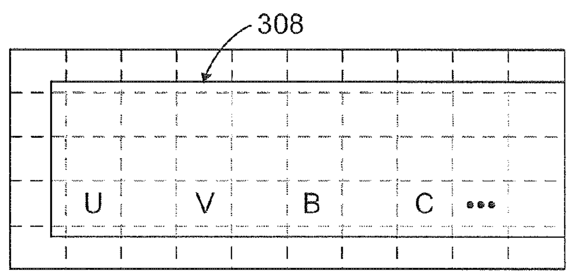
FIGURE 3D
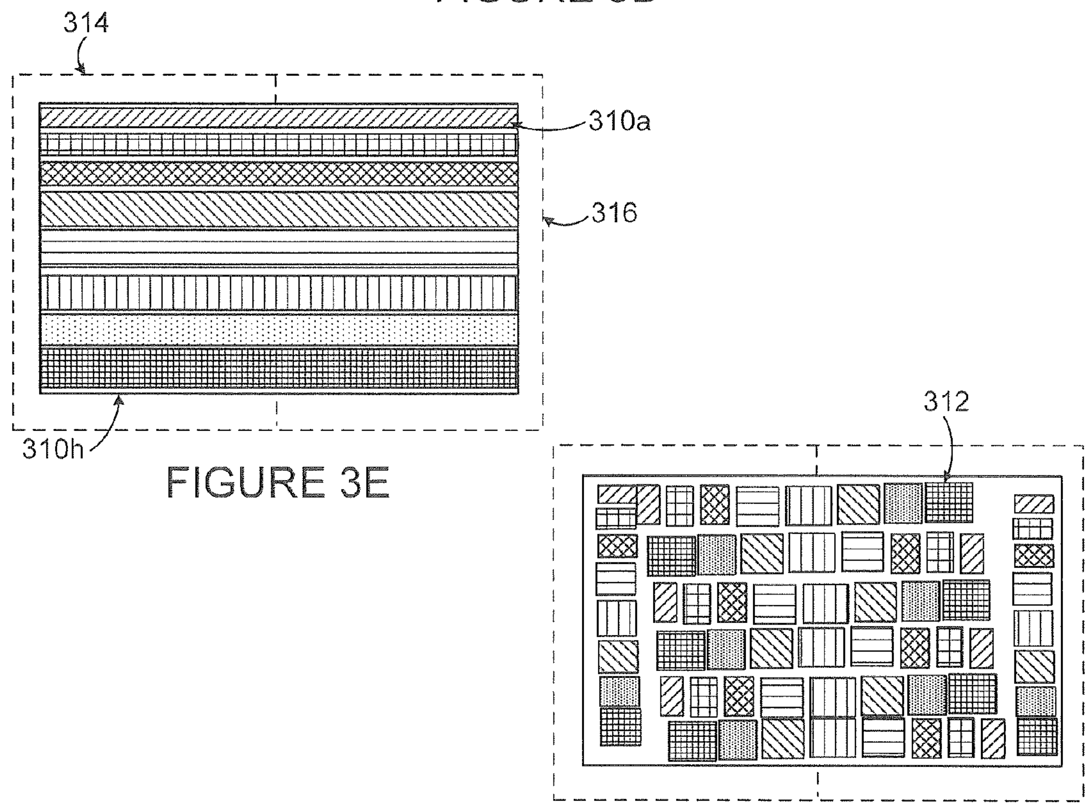
FIGURE 3E
FIGURE 3F

APPARATUS AND METHOD FOR MEASURING AND/OR CONTROLLING ULTRAVIOLET-ACTIVATED MATERIALS IN A PAPER-MAKING PROCESS

TECHNICAL FIELD

This disclosure relates generally to measurement and/or control systems and more specifically to an apparatus and method for measuring and/or controlling ultraviolet-activated materials in a paper-making process.

BACKGROUND

Paper products are routinely formed using one or more ultraviolet-activated materials, such as fluorescent materials. These ultraviolet-activated materials can serve a wide variety of purposes. For example, fluorescent whitening agents ("FWAs") are often added to paper in order to increase the "whiteness" appearance of the paper. Also, fluorescent materials are often added to paper for security purposes. For instance, visible or invisible ultraviolet-fluorescent fibres, pigments, highlights, and planchettes are often added to paper for use in the authentification of paper documents. As particular examples, invisible and visible fibers can be added to paper in an array of colors, lengths, and densities. Also, small particles can be added to paper in order to create highlights that have visible, visible fluorescent, or invisible fluorescent colors. Planchettes represent very small discs that can be embedded into paper during production and are available in visible, visible fluorescent, and invisible fluorescent colors.

Fluorescent materials can be used in various other ways. For example, fluorescent materials could be used to determine the "goodness" of the bonding of a specific material onto fibers or fillers in a papermaking system. This goodness is commonly quantified as a paper substrate's "retention" when discussing the wet-end process of the papermaking system. Fluorescent materials may also be used to analyze the goodness of mixing processes in the papermaking system. In addition, fluorescent materials can be activated by the presence of specific chemicals in the wet-end process of the papermaking system.

SUMMARY

This disclosure provides an apparatus and method for measuring and/or controlling ultraviolet-activated materials in a paper-making process.

In a first embodiment, a method includes illuminating a mixture of materials in a wet-end of a paper process, where the mixture includes an ultraviolet-activated material. The method also includes measuring light from the mixture and determining a property of the ultraviolet-activated material based on the measured light from the mixture.

In particular embodiments, illuminating the mixture includes illuminating the mixture using light in an excitation band associated with the ultraviolet-activated material. Also, measuring the light from the mixture includes measuring light in an emission band associated with the ultraviolet-activated material.

In other particular embodiments, determining the property of the ultraviolet-activated material includes determining a quantity of fluorescent material in recycled material used to form stock for a paper machine and/or determining a quantity of fluorescent material in stock provided to a headbox in the paper process.

In yet other particular embodiments, the method also includes adjusting an operation in the wet-end of the paper process based on the determined property of the ultraviolet-activated material. Adjusting the operation in the wet-end of the paper process could include adjusting an amount of one or more materials used to form stock provided to a headbox in the paper process. The one or more materials used to form the stock could include one or more fluorescent whitening agent(s), fixative(s), fluorescent fiber(s), fluorescent pigment(s), fluorescent particle(s), fluorescent highlight(s), fluorescent planchette(s), and/or fluorescent quenchers.

In still other particular embodiments, the method also includes illuminating a paper product produced using the paper process, where the paper product includes the ultraviolet-activated material. The method further includes measuring second light from the paper product and determining a property of the ultraviolet-activated material in the paper product based on the measured second light from the paper product. In addition, the method includes adjusting an operation in the wet-end of the paper process based on the determined property of the ultraviolet-activated material in the mixture and the determined property of the ultraviolet-activated material in the paper product. Determining the property of the ultraviolet-activated material in the paper product may include determining a spatial distribution and/or an average distribution in the paper product of a fluorescent material or of a material whose light absorption or light scattering properties are modified under ultraviolet illumination. Also, adjusting the operation in the wet-end of the paper process may include adjusting a mixing condition in a blend chest in the wet-end and/or adjusting a fiber or pigment slurry provided to a blend chest in the wet-end.

In a second embodiment, an apparatus includes at least one light emitting diode configured to illuminate a mixture of materials in a wet-end of a paper process using first light, where the mixture includes an ultraviolet-activated material. The apparatus also includes at least one detector configured to measure second light from the mixture, the second light based on the first light. In addition, the apparatus includes at least one controller configured to determine a property of the ultraviolet-activated material based on the measured second light.

In a third embodiment, a method includes illuminating a paper product produced using a paper process, where the paper product includes an ultraviolet-activated material. The method also includes measuring light from the paper product and determining a property of the ultraviolet-activated material in the paper product based on the measured light from the paper product.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIGS. 3A through 3F illustrate example wavelength selectable bandpass filters according to this disclosure;

DETAILED DESCRIPTION

FIGS. 1A through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1A:
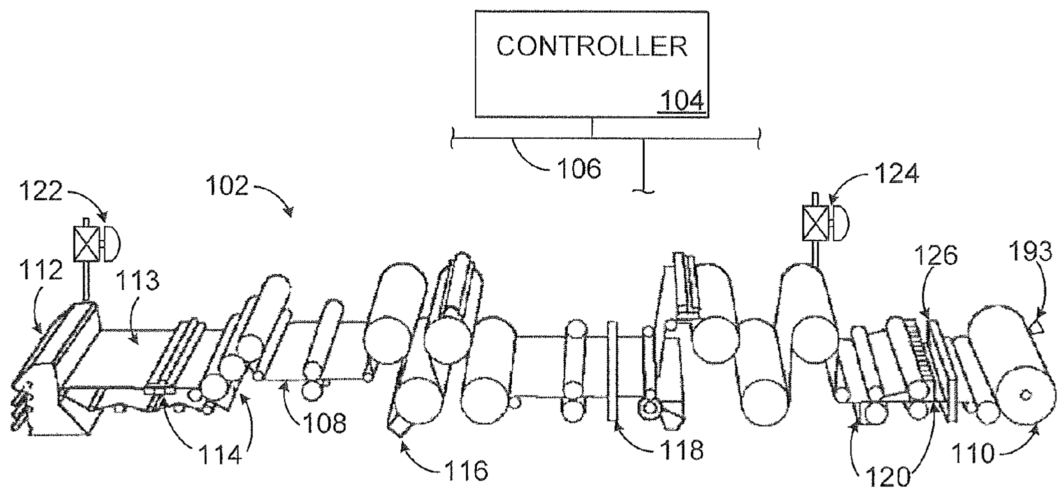
FIGS. 1A and 1B illustrate an example paper production system according to this disclosure.
Figure 1B:
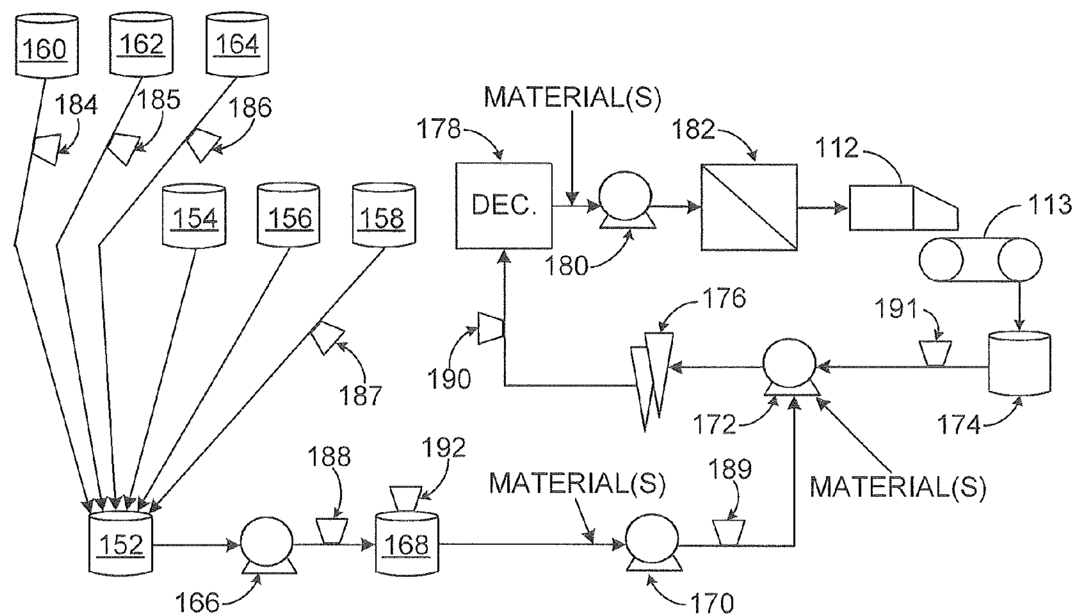

FIGS. 1A and 1B illustrate an example paper production system 100 according to this disclosure. The embodiment of the paper production system 100 shown in FIGS. 1A and 1B is for illustration only. Other embodiments of the paper production system 100 may be used without departing from the scope of this disclosure.

As shown in FIG. 1A, the paper production system 100 includes a paper machine 102, a controller 104, and a network 106. The paper machine 102 includes various components used to produce a paper product. In this example, the various components may be used to produce a paper sheet 108 collected at a reel 110. The controller 104 monitors and controls the operation of the system 100, which may help to maintain or increase the quality of the paper sheet 108 produced by the paper machine 102.

In this example, the paper machine 102 includes a headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water or a suspension of different composition into the pulp suspension across the sheet. The dilution water may be used to help ensure that the resulting paper sheet 108 has a more uniform basis weight or more uniform composition across the sheet 108. The headbox 112 may also include an array of slice lip actuators, which controls a slice opening across the machine from which the pulp suspension exits the headbox 112 onto the moving wire screen or mesh 113. The array of slice lip actuators may also be used to control the basis weight of the paper or the distribution of fiber orientation angles of the paper across the sheet 108.

An array of drainage elements 114, such as vacuum boxes, removes as much water as possible. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of water from the paper sheet 108. An array of rewet shower actuators 118 adds small droplets of water (which may be air atomized) onto one or both surfaces of the paper sheet 108. The array of rewet shower actuators 118 may be used to control the moisture profile of the paper sheet 108, reduce or prevent over-drying of the paper sheet 108, correct any dry streaks in the paper sheet 108, or enhance the effect of subsequent surface treatments (such as calendering).

The paper sheet 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108 and transfers heat energy to it. The arrays of induction heating actuators 120 may therefore be used to control the caliper (thickness) profile of the paper sheet 108. The nips of a calender may also be equipped with other actuator arrays, such as arrays of air showers or steam showers, which may be used to control the gloss profile or smoothness profile of the paper sheet.

Two additional actuators 122-124 are shown in FIG. 1A. A thick stock flow actuator 122 controls the consistency of the incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators may be used for controlling the dry weight and moisture of the paper sheet 108. Additional components could be used to further process the paper sheet 108, such as a supercalender (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper sheets and could be used with systems that process the paper sheets or with systems that produce or process other paper products.

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102 and its associated wet-end (shown in FIG. 1B). This may help to compensate for any variations of the sheet properties from desired targets, which may help to ensure the quality of the sheet 108.

As shown in FIG. 1A, the paper machine 102 includes a scanner 126, which may include one or more sensors. The scanner 126 is capable of scanning the paper sheet 108 and measuring one or more characteristics of the paper sheet 108. For example, the scanner 126 could include sensors for measuring the weight, moisture, caliper (thickness), gloss, color, smoothness, or any other or additional characteristics of the paper sheet 108. The scanner 126 includes any suitable structure or structures for measuring or detecting one or more characteristics of the paper sheet 108, such as sets or arrays of sensors.

The stock provided to the headbox 112 can be produced as shown in FIG. 1B, which may illustrate the "wet-end" of the paper-making process. Here, a blend chest 152 is used to blend materials from various sources. For example, the blend chest 152 could blend wood fibers from a hardwood chest 154, a softwood chest 156, and a broke chest 158. The hardwood chest 154 generally provides wood fibers from hard wood species (such as birch and aspen), while the softwood chest 156 generally provides wood fibers from soft wood species (such as spure and pine). The broke chest 158 generally provides wood fibers from recycled materials, such as recycled paper products or off-specification products produced by the paper machine 102 that have been re-pulped. In general, different paper products produced by the paper machine 102 are associated with different recipes, which can identify quantities of hard and soft wood fibers and provide limits on the amount of broke material that can be used.

The blend chest 152 could also receive additional materials from other sources. For example, the blend chest 152 could receive fluorescent security fibers from a source 160, fluorescent security pigments from a source 162, or fluorescent security particles (such as nano-particles) from a source 164. Any other or additional materials could be received by the blend chest 152.

The blend chest 152 operates to mix various materials together to produce a generally consistent output mixture. The output mixture may represent a thick stock that is further processed to produce the stock provided to the headbox 112. The blend chest 152 includes any suitable structure for mixing materials. Although a single blend chest 152 is shown in FIG. 1B, multiple blend chests 152 could be used. Also, each of the chests 154-158 and sources 160-164 represents any suitable structure providing material to the blend chest 152.

The output mixture from the blend chest 152 is provided by a pump 166 to a machine chest 168. The machine chest 168 generally operates to maintain stock at a constant pressure to a pump 170. The machine chest 168 could also dilute the mixture from the blend chest 152, typically by a relatively small amount. The machine chest 168 is traditionally separate from the blend chest 152, although the functions of the machine chest 168 could also be performed by the blend chest 152. The pumps 166 and 170 represent any suitable pumps, such as stock pumps. The mixture from the machine chest 168 is mixed with one or more dyes, fluorescent whitening agents, fluorescent pigments, fluorescent colorants, fluorescent quenchers (for reducing fluorescence), or other materials at the pump 170.

The mixture provided by the pump 170 is received at a pump 172, along with water from a white water chest 174 (and possibly additional colorants or other materials, including fluorescent ones). The white water chest 174 provides water for mixing with the material from the pump 170, thereby producing a thinner stock used by the headbox 112. The white water chest 174 represents any suitable structure for providing water used to form stock for a paper machine. Also, the pump 172 represents any suitable pump, such as a fan pump.

The stock from the pump 172 is provided to one or more cleaners 176, which can purify the stock and remove unwanted materials from the stock. The cleaners 176 could, for example, represent conical or partly cylindrical devices for removing grit from the stock. The cleaned stock is provided to a deculator 178, which can remove entrained and dissolved air from the stock. A pump 180 provides stock from the deculator 178, which can be mixed with additional dyes or other materials, to a screen 182. The pump 180 represents any suitable pump, such as a headbox feed pump. The screen 182 is typically used to remove larger particles and flakes from the stock. The screened stock is then provided to the headbox 112 for use in forming a paper sheet 108 or other product.

As shown here, the materials used to form the stock for the headbox 112 can come from a variety of sources, including broke (recycled) materials. Often times, these broke materials include some form of ultraviolet-activated material (such as fluorescent whitening agents or other fluorescent material), and the amount of ultraviolet-activated material could vary depending on the broke materials being recycled. Also, certain applications (such as the formation of paper currency) could have strict guidelines regarding the use of ultraviolet-activated material. For instance, there could be various requirements regarding the quantity of fluorescent pigments or fibers used in a specified area of paper currency, as well as requirements regarding the length and thickness of fluorescent fibers.

Conventional paper mills often measure the color (including the fluorescence) of a final paper product, such as at the reel 110 of the paper machine 102. This allows the paper mills to verify whether the finished product does or does not meet color specifications or other requirements. However, this technique is often not able to make adequate adjustments to the system 100 in order to increase or guarantee compliance with the specifications. For example, this technique is often too slow in responding to abrupt changes in the composition of the broke material. As a result, this technique could allow an excessive amount of product to be produced that is outside of the product's desired or required specifications.

To support better use of ultraviolet-activated materials in the system 100, the system 100 may include one or more sensors 184-192, which could be distributed in the wet-end of the paper-making process. The system 100 may also include one or more sensors 193 at the reel 110 of the paper-machine 102. These sensors 184-193 could be used to measure various properties of ultraviolet-activated materials at those locations. For example, the sensors 184-193 could be used to determine the quantity of fluorescent materials at various stages of the wet-end and in the final paper product. Other properties of the fluorescent materials could also be determined. These properties could be used by the controller 104 to control the system 100. Among other things, this may allow the system 100 to respond more rapidly to changes in the composition of the broke material or in other materials provided to the blend chest 102. Each of the sensors 184-193 includes any suitable structure(s) for measuring one or more properties of at least one ultraviolet-activated material. Example embodiments of the sensors 184-193 are described below with respect to FIGS. 2 through 4D, although any other or additional sensors could be used.

In some embodiments, each of the sensors 184-193 could include one or more light emitting diodes (LEDs) or other illumination sources. For example, each of the sensors 184-193 could include one or more ultraviolet light emitting diodes, each of which could emit light in a single wavelength band. Other light emitting diodes could also be used, such as light emitting diodes that emit light in the visible spectrum. The light emitted by the light emitting diodes could vary depending on, for example, the excitation bands of one or more fluorescent materials being measured.

Each of the sensors 184-193 could also include one or more detectors, which can measure light reflected from, emitted by, or transmitted through material being examined. The detectors could, for example, measure the intensity of light in one or more ultraviolet and/or visible wavelength bands, such as in the emission bands of various fluorescent materials. The emission bands could include wavelengths such as 440 nm, 530 nm, 620 nm, or even wavelengths in the ultraviolet spectrum. In some embodiments, the detectors could also measure light in one or more reference bands, allowing the detector measurements to be scaled appropriately. If multiple fluorescent materials having the same excitation band and different emission bands may be present, at least three centroid bandpass filters can be used in the detectors, and the detectors could take measurements in the reference band(s) and at each of the potential emission bands. As a particular example, the detectors could measure the intensity of light in 20 nm bands that are centered at or that include one or more of 350 nm, 400 nm, 450 nm, 500 nm, 550 nm, 600 nm, 650 nm, 700 nm, and 750 nm, as well as in bands that include the typical emission peak wavelength(s) of fluorescent material(s) and a reference (non-fluorescent) band.

Any suitable geometry could be used with the illumination sources and the detectors in the sensors 184-193. For example, the sheet 108 or other material could be illuminated at 0° and measured at 0° (denoted 0/0), illuminated at 80° and measured at 0° (denoted 80/0), or illuminated at 70° and measured at 70° (denoted 70/70). Any other angle(s) could be used for the illumination and/or detection performed by the sensors 184-193, and the sensors 184-193 may or may not use the same angles.

The controller 104 receives measurement data from the scanner 126 and the sensors 184-193 and uses the data to control the system 100. For example, the controller 104 may use the measurement data to adjust the various actuators in the paper machine 102 so that the paper sheet 108 has properties at or near desired properties. The controller 104 may also make various adjustments to the wet-end, thereby altering the production of the stock used by the headbox 112 to produce the paper sheet 108. The controller 104 includes any hardware, software, firmware, or combination thereof for controlling the operation of at least part of the system 100. Also, while one controller is shown here, multiple controllers could be used, such as one or more controllers for controlling the paper machine 108 and one or more controllers for controlling the wet-end.

In some embodiments, the controller 104 can use measurements from the sensors 184-193 to determine one or more characteristics of ultraviolet-activated material(s) in the sheet 108 and in different areas of the wet-end. For example, the controller 104 could determine average fluorescent quantities of specific materials in or on the sheet 108. The controller 104 could also determine the spatial distribution of specific fluorescent materials in or on the sheet 108 (such as the distribution of fluorescing fibers and pigments on the paper). The controller 104 could then adjust the operation of the system 100 so that, for example, the average quantity or spatial distribution of the fluorescent materials satisfies desired specifications.

As another example, the sensor 191 could be used to analyze and define the retention of dosed fluorescent materials. If the sensor 191 measures no dosed fluorescent materials, the retention can be nearly 100%. This retention analysis may be used, among other things, to analyze the bonding of a fluorescent material into the fibres and/or fillers and to control fixative or ionic balance.

The network 106 is coupled to the controller 104 and various components of the system 100 (such as the actuators, scanners, and sensors). The network 106 facilitates communication between components of system 100. The network 106 represents any suitable network or combination of networks facilitating communication between components in the system 100. The network 106 could, for example, represent an Ethernet network, an electrical signal network (such as a HART or FOUNDATION FIELDBUS network), a pneumatic control signal network, or any other or additional network(s).

Although FIGS. 1A and 1B illustrate one example of a paper production system 100, various changes may be made to FIGS. 1A and 1B. For example, other systems could be used to produce paper sheets or other products. Also, while shown as including a single paper machine 102 with various components and a single controller 104, the production system 100 could include any number of paper machines or other production machinery having any suitable structure, and the system 100 could include any number of controllers. Further, any other or additional components could be used for preparing the stock used by the paper machine 102 to produce the sheet 108. In addition, FIGS. 1A and 1B illustrate one operational environment in which measurement and control of ultraviolet-activated materials in paper products can be used. This functionality could be used in any other suitable system.

Figure 2:
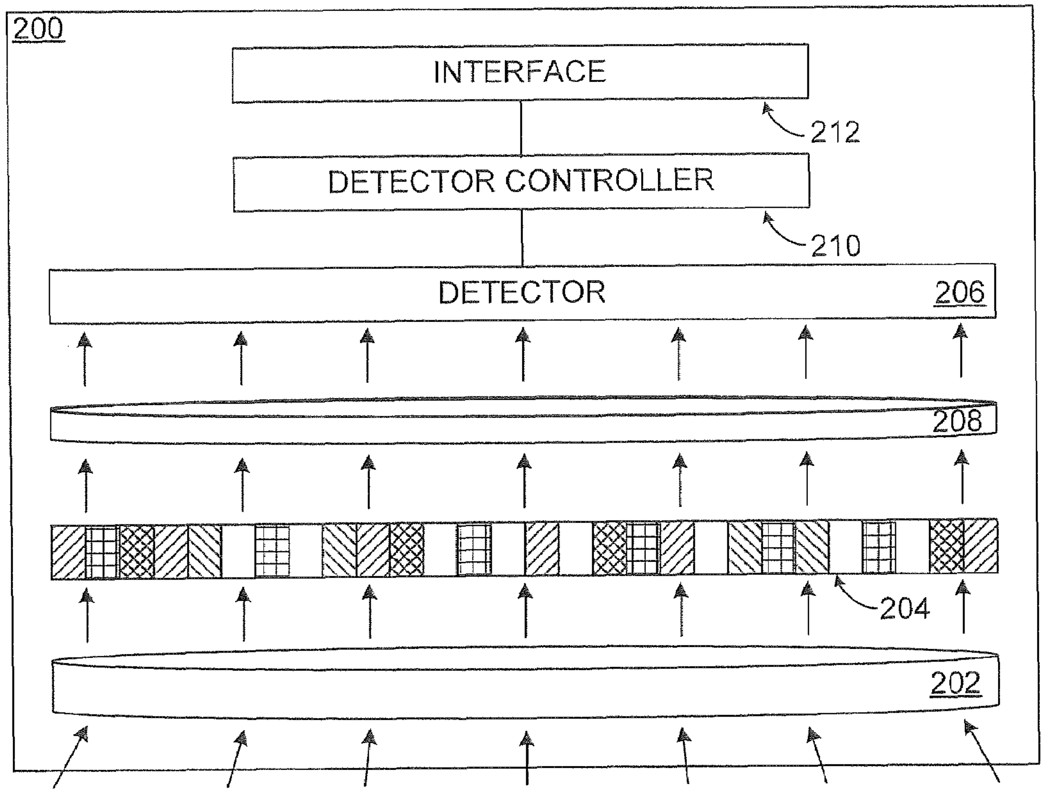
FIG. 2 illustrates an example mechanism for measuring ultraviolet-activated materials in a paper-making process according to this disclosure.

FIG. 2 illustrates an example mechanism for measuring ultraviolet-activated materials in a paper-making process according to this disclosure. In particular, FIG. 2 illustrates an example camera-based color sensor 200 that can be used to identify one or more properties of ultraviolet-activated materials in a paper-making process. The embodiment of the camera-based color sensor 200 shown in FIG. 2 is for illustration only. Other embodiments of the camera-based color sensor 200 could be used without departing from the scope of this disclosure.

As shown in FIG. 2, light transmitted through, emitted by, or reflected from a paper sheet 108 or other material being examined can be received at optics 202. The optics 202 alter the light received at the color sensor 200, such as by focusing or diffusing the light. The optics 202 can perform any other or additional functions depending on the implementation. The optics 202 include any suitable structure(s), such as one or more lenses, mirrors, or diffusers.

Light from the material being examined passes through a wavelength selectable bandpass filter 204. The wavelength selectable bandpass filter 204 includes different regions that filter different wavelengths of light. This allows light in different wavelength bands to pass through the different regions of the filter 204. For example, different regions of the wavelength selectable bandpass filter 204 could filter the light into different bands that are 20 nanometers wide. As particular examples, regions in the wavelength selectable bandpass filter 204 could filter light into different 20 nanometer-wide bands centered at or including one or more of 350 nm, 400 nm, 450 nm, 500 nm, 550 nm, 600 nm, 650 nm, 700 nm, and 750 nm. Additional bands could be centered at or include wavelengths associated with fluorescence, such as 280 nm, 360 nm, or 440 nm. The wavelength selectable bandpass filter 204 includes any suitable structure(s) for filtering light into different wavelength bands. Example embodiments of the wavelength selectable bandpass filter 204 are shown in FIGS. 3A through 3F, which are described below.

The filtered wavelength bands are received at a detector 206. The detector 206 is capable of measuring an intensity of light in the various wavelength bands provided by the wavelength selectable bandpass filter 204. For example, the detector 206 could include an array or matrix of smaller detectors, such as an array or matrix of pixels. Each detector in the array or matrix could be used to measure the intensity of light provided in one of the wavelength bands. By using multiple detectors to measure light in multiple wavelength bands, spectral information about the material being examined can be obtained, allowing one or more properties of ultraviolet-activated materials to be determined. For instance, multiple detectors in the array or matrix could simultaneously measure light in multiple wavelength bands, including the wavelength bands associated with fluorescence. The detector 200 includes any suitable structure(s) for measuring light in multiple wavelength bands. The detector 200 could, for example, represent a charge-coupled device (CCD), a complimentary metal oxide semiconductor (CMOS) device, or a charge injection device (CID).

Micro-optics 208 could be used to focus light from the wavelength selectable bandpass filter 204 onto individual pixels or other structures of the detector 206. The micro-optics 208 include any suitable structure(s), such as micro-lenses formed on the surface of the detector 206.

A detector controller 210 is coupled to and controls the operation of the detector 206. For example, the detector controller 210 could cause the detector 206 to begin measuring light and to stop measuring light in wavelength bands provided by the wavelength selectable bandpass filter 204. The detector controller 210 could also receive measurement data from the detector 206 and provide the measurement data to an external component, such as the controller 104. The detector controller 210 could perform any other or additional actions to facilitate operation of the detector 206. The detector controller 210 includes any suitable structure(s) for controlling the operation of one or more detectors.

An interface 212 can be used to facilitate communication between the color sensor 200 and an external component, such as the controller 104. The interface 212 could support communications over any suitable type of communication medium, such as a wired or wireless network or link. The interface 212 includes any suitable structure supporting communication with the color sensor 200. As particular examples, the interface 212 could support communications over a Universal Serial Bus (USB) link, a FireWire link, or a gigabit Ethernet link.

In some embodiments, the entire color sensor 200 could be implemented using a digital camera or other digital imaging device. In general, a "digital imaging device" represents any digital device designed to capture visual information using individual pixels or other image capturing elements. In these embodiments, a custom filter (the wavelength selectable bandpass filter 204) can be used in front of the camera's pixels or other image capturing elements (the detector 206) to enable the camera to be utilized as a color analyzer/sensor. Conventional digital cameras typically use red-green-blue (RGB) or cyan-magenta-yellow (CMY) filters, which are inappropriate for calorimetric measurements. The wavelength selectable bandpass filter 204 provides proper wavelength bands for spectral analysis and color determinations (including fluorescence measurements). The wavelength bands could represent any suitable wavelength bands, whether in the ultraviolet, visible, near infrared, infrared, or other spectrums.

Digital cameras may be less expensive than other color measurement techniques, such as those using expensive diffraction grating spectrometers. Also, the wavelength selectable bandpass filter 204 could be removable, allowing different wavelength selectable bandpass filters 204 to be inserted into and used in the color sensor 200. This would allow the same overall color sensor structure to be reused for various types of measurements, further reducing costs to users of the color sensors. Further, since small wavelength bands are measured in the color sensor 200, the color sensor 200 could reduce signal-to-noise ratios in the color measurements. In addition, the color sensor 200 could be smaller than conventional color measuring devices, enabling the color sensor 200 to be used in space-confined applications.

In particular embodiments, a digital camera could be fabricated with the wavelength selectable bandpass filter 204. For example, the wavelength selectable bandpass filter 204 could be formed as part of the detector 206, such as during formation of a CCD, CMOS, or CID-based detector 206. In other particular embodiments, the wavelength selectable bandpass filter 204 could be retrofitted into an existing digital camera. For instance, the cover glass or infrared block on a digital camera could be replaced with the wavelength selectable bandpass filter 204. A digital camera incorporating the wavelength selectable bandpass filter 204 could be produced in any other suitable manner.

Although FIG. 2 illustrates one example of a mechanism for measuring ultraviolet-activated materials in a paper-making process, various changes may be made to FIG. 2. For example, the color sensor 200 may or may not require optics 202, 208. Also, various embodiments of the wavelength selectable bandpass filter 204 could be used, and the different filtering regions of the wavelength selectable bandpass filter 204 may be arranged in a pattern or arranged randomly or pseudo-randomly.

FIGS. 3A through 3F illustrate example wavelength selectable bandpass filters according to this disclosure. The wavelength selectable bandpass filters could, for example, be used in the camera-based color sensor 200 of FIG. 2. The embodiments of the wavelength selectable bandpass filters shown in FIGS. 3A through 3F are for illustration only. Other embodiments of the wavelength selectable bandpass filter could be used without departing from the scope of this disclosure.

Figure 3A:
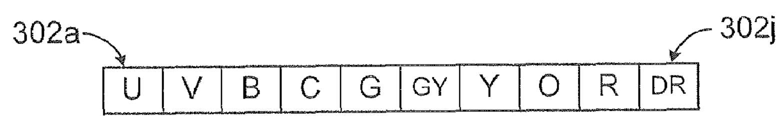

As shown in FIG. 3A, a wavelength selectable bandpass filter includes a single row of pixel masks 302*a*-302*j*, each of which is designed to pass a different wavelength band of light. For example, the pixel masks 302*a*-302*j* could be respectively designed to pass light in the following bands of the spectrum: ultraviolet (U), violet (V), blue (B), cyan (C), green (G), green-yellow (GY), yellow (Y), orange (O), red (R), and deep red (DR). Each of these pixel masks 302*a*-302*j* can filter light passing through it so that only light falling into one of these wavelength bands is passed. Various pixels or other detectors could then be used to measure the intensity of light in each of the wavelength bands, allowing the color of material to be determined. In this example, each of the pixel masks 302*a*-302*j* is aligned with a single pixel or other detector. Also, while shown as a single row of pixel masks 302*a*-302*j*, this row could be replicated any number of times (whether the order of the pixel masks 302*a*-302*j* in the rows remains the same or changes). In addition, the ultraviolet wavelength band(s) could include one or more wavelengths associated with fluorescence.

Figure 3B:
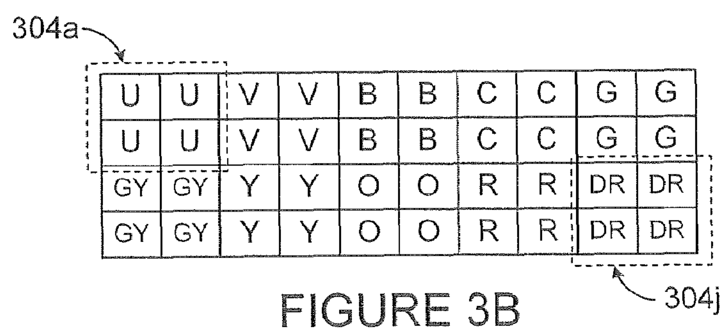

As shown in FIG. 3B, a wavelength selectable bandpass filter includes blocks 304*a*-304*j* of pixel masks, each block representing a 2×2 block of pixel masks. The blocks 304*a*-304*j* are designed to pass different wavelength bands to multiple sets of pixels or other detectors (in this case, four pixels per block). This allows multiple measurements to be taken of light passing through each of the blocks 304*a*-304*j*, which may allow, for example, an average measurement value to be determined for each of the wavelength bands. Again, the structure in FIG. 3B could be replicated any number of times (whether the order of the pixel blocks 304*a*-304*j* remains the same or changes), and the ultraviolet wavelength band(s) could include one or more wavelengths associated with fluorescence.

As shown in FIG. 3C, a wavelength selectable bandpass filter includes discrete masks 306*a*-306*c*. The discrete masks 306*a*-306*c* are designed to pass different wavelength bands to pixels or other detectors. In this example, the masks 306*a*-306*c* are not aligned with pixels or other individual detectors (the pixels are denoted with dashed lines), and light from each of the masks 306*a*-306*c* may fall completely or partially on a pixel. The pixels partially receiving light may or may not be used to generate measurement data. While only three discrete masks are shown in FIG. 3C, other discrete masks could be used for the other wavelength ranges described above. Also, multiple masks could be used for each wavelength band.

As shown in FIG. 3D, a wavelength selectable bandpass filter includes a linear variable filter 308, which can be placed over a number of pixels or other detectors. The linear variable filter 308 generally transitions in its filtering function, allowing light in one wavelength band to pass in one area of the filter 308 and allowing light in another wavelength band to pass in a different area of the filter 308. Although not shown, the linear variable filter 308 could transition and allow light to pass in all of the wavelength bands noted above. Also, one or multiple linear variable filters 308 could be used. In some embodiments, a linear variable filter 308 could be formed by applying a suitable coating on the surface of the detector 206 or on the surface of a glass cover of the detector 206. In particular embodiments, a linear variable filter 308 could be limited to use with visible light, and additional structures could be used to allow other narrow bands of light to pass (such as ultraviolet bands). For example, a glass doped with Holmium or Neodymium could be used to pass particular known groups of narrow wavelength bands for wavelength calibration or other purposes.

In FIG. 3E, a wavelength selectable bandpass filter includes multiple filters or regions 310*a*-310*h*, each of which may be aligned with or otherwise associated with one or multiple rows of pixels or other detectors. Each one of these regions 310*a*-310*h* could pass a different wavelength band of light, such as one of the wavelength bands discussed above. The regions 310*a*-310*h* could have any suitable size and shape, and the regions 310*a*-310*h* may or may not have the same size or shape.

In FIG. 3F, a wavelength selectable bandpass filter includes multiple filters or regions 312, each of which may be aligned or otherwise associated with one or multiple pixels or other individual detectors. Each of these regions 312 could pass a different wavelength band of light, such as one of the wavelength bands discussed above. The regions 312 could have any suitable size and shape, and the regions 312 may or may not have the same size or shape. The arrangement of the regions 312 could be periodic, random, or pseudo-random.

In these various embodiments, the wavelength selectable bandpass filter is used to allow light in different narrow wavelength bands to reach different pixels or other portions of the detector 206. This allows the detector 206 to measure the spectrum of light coming from the material being examined. The wavelength bands passed by the wavelength selectable bandpass filter could represent any suitable bands, such as different 20 nanometer-wide bands centered at or including one or more of 350 nm, 400 nm, 450 nm, 500 nm, 550 nm, 600 nm, 650 nm, 700 nm, and 750 nm. Other wavelength bands could also be provided by the wavelength selectable bandpass filter and measured by the detector 206, such as wavelength bands associated with fluorescence, reference, and emitted light. In addition, areas of pixels or other individual detectors within the detector 206 could be predefined prior to use, where the areas of pixels or other detectors correspond to the different filtering regions of the wavelength selectable bandpass filter 204.

In some embodiments, the signal-to-noise ratios in the wavelength bands passed from the wavelength selectable bandpass filter could be similar or equal. Also, the sensitivity of the detector 206 may or may not be the same at all wavelength bands. Further, the transmittance of the wavelength selectable bandpass filter may or may not vary as a function of wavelength. Beyond that, the total area of the wavelength selectable bandpass filter used to provide light at a particular wavelength band could be selected in any suitable manner, such as to optimize the signal-to-noise ratio for that wavelength band. In addition, the pattern of the regions used to provide light at particular wavelength bands could be selected based on any suitable criteria, such as the measurement task to be performed. In other embodiments, multiple bandpass filters may be provided, not all of which are simultaneously deployed in front of the detector. In these embodiments, the bandpass filter or set of filters deployed at any time can be selected according to the measurement task to be performed.

As shown in FIGS. 3E and 3F, in some embodiments, the wavelength selectable bandpass filter could be used in conjunction with one or more backings 314-316. For example, a paper sheet 108 or other material could be placed between the backings 314-316 and the wavelength selectable bandpass filter. The paper sheet 108 or other material could be illuminated, and the wavelength selectable bandpass filter could then filter light reflected from the paper sheet 108 or other material over the backings 314-316. In this way, color measurements associated with multiple backings can be captured at the same time. In particular embodiments, the backings 314-316 represent white and black backings. The use of two backings is for illustration only. Any number of backings could be used here, such as when black and white (or other color) backings are arranged in a checkerboard pattern. Also, backings could be used with any of the wavelength selectable bandpass filters shown here or with other wavelength selectable bandpass filters.

As noted above, different types of optics can be used in the color sensor 200, and the use of optics in the color sensor 200 may be optional. If a defocused image of a paper sheet 108, stock, or other material is received at the wavelength selectable bandpass filter, the light in the defocused image could represent the average light from the paper sheet 108, stock, or other material (or a portion thereof). In this case, each filtering region of the wavelength selectable bandpass filter could output the portion of that average light falling within the narrow wavelength band of that region. The measured values produced by the detector 206 could then be used in any suitable manner, such as by summing the measurements for each individual wavelength band to produce improved measurement values.

If a focused image of the paper sheet 108, stock, or other material is received at the wavelength selectable bandpass filter, the light in the image can vary depending on the color of the material in different areas of the focused image. In this case, at least some of the filtering regions of the wavelength selectable bandpass filter could receive light from different areas of the paper sheet 108, stock, or other material. The filtering regions of the wavelength selectable bandpass filter could therefore output light in narrow wavelength bands from different areas of the paper sheet 108, stock, or other material. In this way, the detector 206 could be used, for example, to detect color variations, fluorescent emission variations, or fluorescent material density variations in different areas of the paper sheet 108, stock, or other material. For measurements with different spatial resolutions, corresponding patterns of regions on the bandpass filter and suitable degrees of focusing sharpness (or de-focusing) can be chosen and used.

Although FIGS. 3A through 3F illustrate examples of wavelength selectable bandpass filters 204, various changes may be made to FIGS. 3A through 3F. For example, a wavelength selectable bandpass filter 204 could include any suitable number of regions passing different wavelength bands. Also, each of the regions of the wavelength selectable bandpass filter 204 could have any suitable size and shape, and the regions could have any suitable arrangement. Furthermore, some of the regions of the bandpass filter may pass essentially all wavelength bands. In addition, the use of the backings 314-316 may or may not be needed, depending on the implementation.

FIGS. 4A through 4D illustrate another example mechanism for measuring ultraviolet-activated materials in a papermaking process according to this disclosure. In particular, FIGS. 4A through 4D illustrate an example fluorescence sensor 400 for measuring fluorescent materials. The embodiments of the fluorescence sensor 400 shown in FIGS. 4A through 4D are for illustration only. Other embodiments of the fluorescence sensor 400 could be used without departing from the scope of this disclosure.

As shown in FIGS. 4A through 4D, the fluorescence sensor 400 includes one or more light emitting diodes (LEDs) 402, which are capable of generating light at one or more wavelengths or wavelength bands. The light is used to illuminate a material (such as stock or paper) being examined. For example, the light emitting diodes 402 could emit ultraviolet light at any suitable wavelengths or wavelength bands, including in the UV(A), UV(B), and/or UV(C) bands. As particular examples, one or more of the light emitting diodes 402 could emit ultraviolet light having one or more of the following wavelengths: 205 nm, 250 nm, 280 nm, 300 nm, 360 nm, and 380 nm. The light emitting diodes 402 could also emit light having one or more reference wavelengths or wavelength bands. The light emitting diodes 402 could represent any suitable number and type of light emitting diode(s) for generating light at any suitable wavelengths or wavelength ranges, including regular LEDs, organic LEDs (OLEDs), and flashing LEDs (FLEDs).

An LED controller 404 is coupled to and controls the operation of the light emitting diodes 402. For example, the LED controller 404 could turn the light emitting diodes 402 on and off and vary the current provided to the light emitting diodes 402. The LED controller 404 could also control the cooling of the light emitting diodes 402 or any other or additional aspects of the light emitting diodes' operation. Depending on the implementation, the LED controller 404 could further control the wavelength or wavelength band of the light emitted by the light emitting diodes 402. The LED controller 404 includes any suitable structure for controlling one or more light emitting diodes.

Optics 406 can be used to control the illumination of the material being examined. The optics 406 could, for example, focus the emitted light from the light emitting diodes 402 onto the material or diffuse the emitted light. The optics 406 include any suitable structure(s) for controlling the illumination of the material, such as one or more lenses, mirrors, or diffusers. Similarly, optics 408 can be used to control radiances reflected from the material being examined, such as by focusing the radiances. The optics 408 include any suitable structure(s), such as one or more lenses or diffusers.

One or more detectors 410 measure the radiances reflected or otherwise provided by the material being examined. For example, the detectors 410 could measure the intensity of the radiances at certain ultraviolet or other wavelengths or wavelength bands. As a particular example, one or more detectors 410 could measure the intensity of ultraviolet light having one or more of the following wavelengths: 205 nm, 250 nm, 280 nm, 300 nm, 360 nm, and 380 nm. One or more detectors 410 could also measure the intensity of light at one or more fluorescent materials' emission wavelength(s), such as 440 nm. One or more detectors 410 could further measure the intensity of reference light. The measurement(s) of the reference light could occur using light reflected from the material being examined or by directly sampling the reference light emitted by the light emitting diodes 402. A detector 410 could measure the intensity of light at one or multiple wavelengths or wavelength bands.

In some embodiments, at least one detector 410 measures light from stock or paper being examined at the same wavelengths as the light emitted by the light emitting diodes 402, as well as at higher wavelengths associated with fluorescence emissions by components of the stock or paper. For example, at least one detector 410 could have a detection wavelength band at one or more excitation bands (such as 280 nm) and at one or more emission bands (such as 360 nm and/or 410 nm). In particular embodiments, between two and five ultraviolet wavelengths or wavelength bands can be emitted and measured, and between one to four reference wavelengths can be emitted and measured.

Each detector 410 includes any suitable structure or structures for measuring light. Each detector 410 could, for example, include a spectrometer covering an illumination wavelength or wavelength band and a higher wavelength or wavelength band, a photomultiplier tube with or without a band filter, or an LED detector. Also, different detectors 410 could be implemented using different components.

Control values for the light emitting diodes 402 can be provided by a controller 412, and measurements from the detectors 410 can be provided to the controller 412. The controller 412 may, among other things, use measurements from the detectors 410 to determine one or more properties of ultraviolet-activated materials in a material being examined. The controller 412 could use these determined properties to estimate the quality of and make adjustments to the system 100. The controller 412 could perform any other or additional actions according to particular needs. The controller 412 includes any hardware, software, firmware, or combination thereof for using measurements related to the properties of stock or paper. In this example, the controller 412 includes at least one processor 414 and at least one memory 416 for storing instructions and data used, generated, or collected by the processor(s) 414. The controller 412 also includes at least one network interface 418 for communicating over a network, such as an Ethernet network or an electrical signal network. The controller 412 in this example could be implemented as part of the controller 104 in FIG. 1A, integrated into another component in the system 100, or used as a stand-alone component in the system 100.

The fluorescence sensor 400 can be used in different ways as shown in FIGS. 4A through 4D. For example, in FIG. 4A, the fluorescence sensor is used to measure one or more properties of a sample/sheet 419 of material. The sample/sheet 419 could, for example, represent a sample of stock in the wet-end of the system 100 or a sample of the sheet 108. The sample/sheet 419 could also represent the sheet 108 itself. The sample 419 could be prepared in any suitable manner, such as by removing the sample 419 from a tank or other storage vessel. The sample 419 could also be prepared in an "off-line" manner (outside of the normal process flow). This could include placing the stock material between layers of material having the same or lower moisture content, forming a pancake-type structure. The sample 419 could be obtained or produced in any other suitable manner.

Figure 4A:
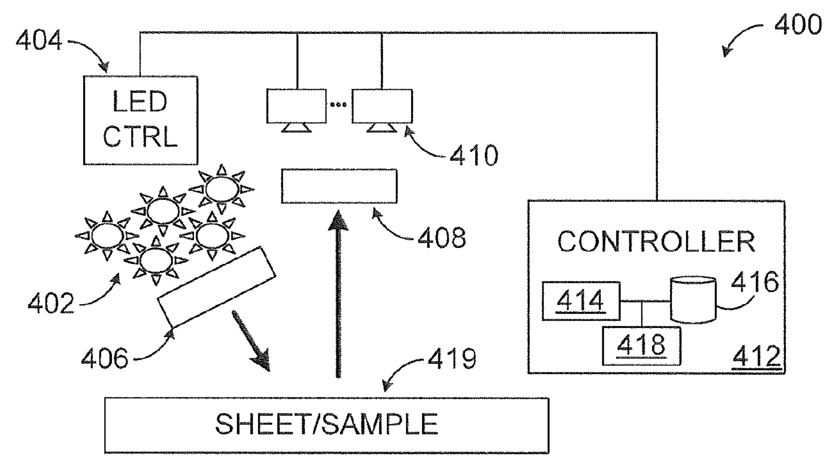
FIGS. 4A through 4D illustrate another example mechanism for measuring ultraviolet-activated materials in a paper-making process according to this disclosure.
Figure 4B:
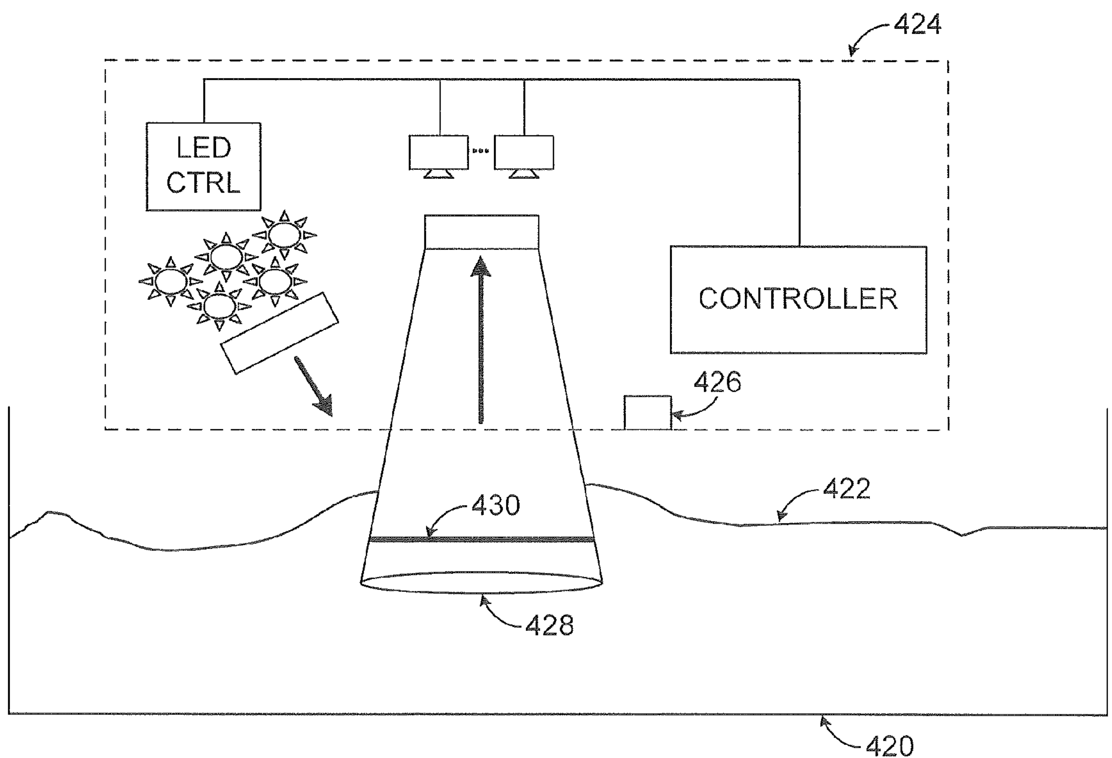

In FIG. 4B, the fluorescence sensor is used in conjunction with a tank 420 containing material 422, such as a tank storing stock that has been mixed (like in the machine chest 168). In some embodiments, at least some of the components 402-412 could be integrated into a gauge 424 or other instrument that cap be placed within the tank 420. In order to help improve measurements, various techniques could be used to compensate for the waves or other disturbances to the surface of the material 422 in the tank 420. For example, a distance sensor 426 could be used to identify the distance between the gauge 424 and the measured surface of the material 422. The identified distance could then be used to compensate for measurements taken by the gauge 424 or to move the gauge 424 within the tank 420 (so that the gauge 424 is at a specified distance from the material 422). As another example, the gauge 424 could include a cup-type structure or other enclosure 428 in which higher-pressure air can be used to control the distance between other gauge components and a controlled surface 430 of the material 422. In particular embodiments, an air bubble within the enclosure 428 can be periodically reformed, which can (among other things) allow a more stable surface 430 to be reformed from time to time.

Figure 4C:
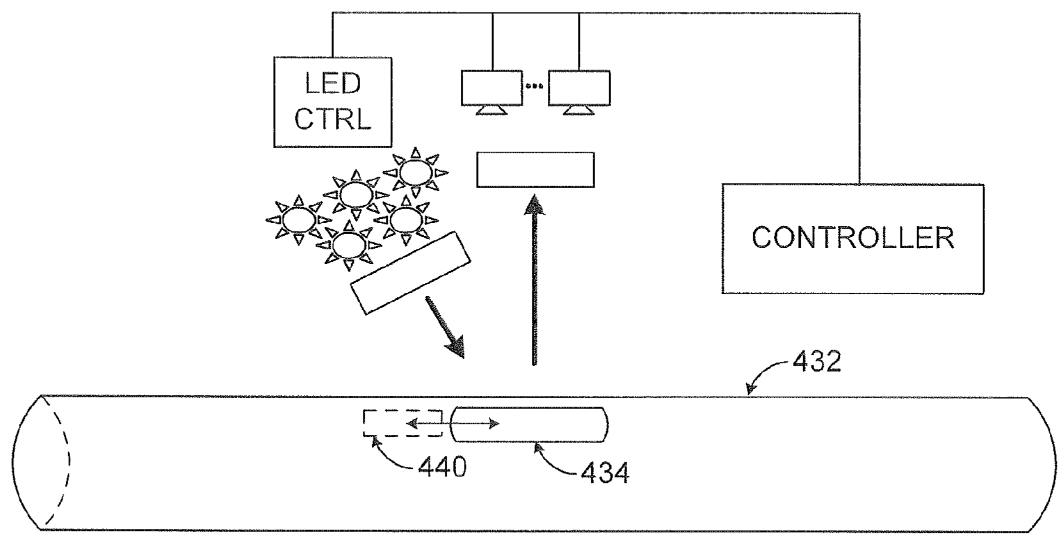

In FIG. 4C, the fluorescence sensor is used in conjunction with a pipe 432, which transports stock or other material from one location to another within the system 100. For example, the fluorescence sensor could take measurements of stock flowing through the pipe 432 through a window 434 in the pipe 432. The window 434 could be formed from any suitable material facilitating illumination and measurement of the material in the pipe 432. The window 434 could, for example, represent UV quartz.

Figure 4D:
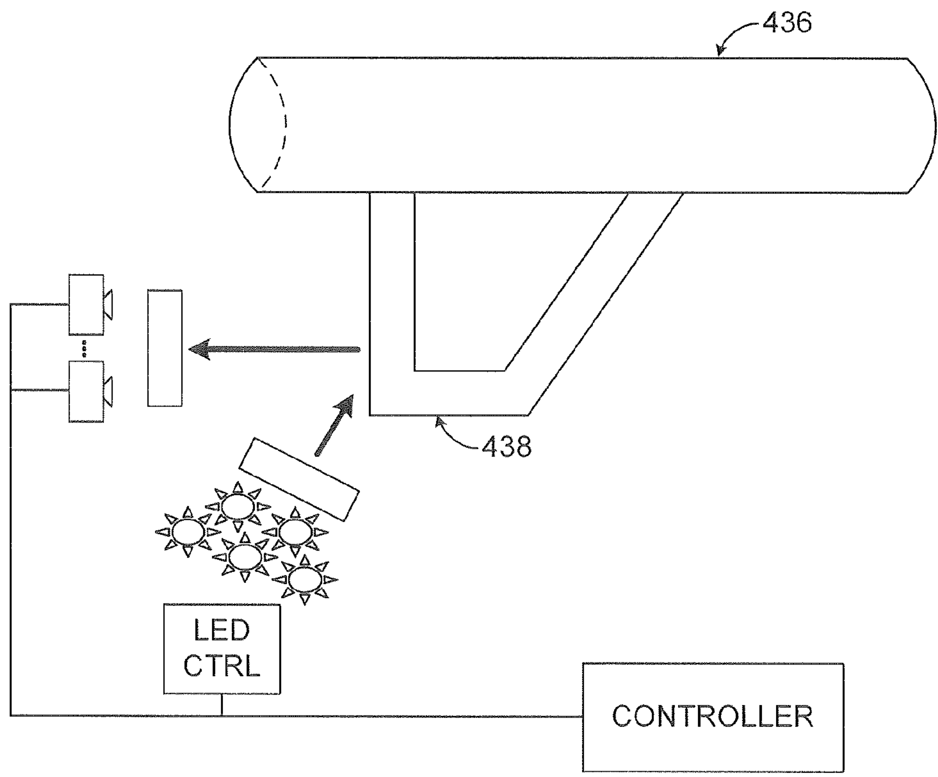

In FIG. 4D, the fluorescence sensor is again used in conjunction with a pipe 436, and the fluorescence sensor takes measurements of material flowing through a sampling pipe 438 (which branches away from and then rejoins the main pipe 436). Again, a window or other structure could be used to allow measurement of the material in the sampling pipe 438.

In any of these embodiments, the fluorescence sensor can be used to take any suitable measurements of stock or paper and to determine one or more properties of the stock or paper. For example, the fluorescence sensor could illuminate the stock or paper with ultraviolet light at one or more wavelengths or wavelength bands. The fluorescence sensor could also illuminate the stock or paper with light at one or more reference wavelengths or wavelength bands. The fluorescence sensor could further take various measurements of light from the stock or paper, such as at the same wavelengths or wavelength bands as the light emitted by the light emitting diodes 402 and at any wavelengths or wavelength bands associated with fluorescence of the stock or paper. Based on these measurements, the controller 412 can perform any suitable calculations to determine one or more properties of the fluorescent materials in the stock or paper. In this way, determinations can be made regarding, for example, the quantity of fluorescent material in stock provided to the paper machine 102. This can also be used to make adjustments to the stock preparation performed in the wet-end of the system 100.

It may be noted that the light emitting diodes 402 and the detectors 410 can be arranged in any suitable manner, such as by arranging each in a circle. Also, the light emitting diodes 402 could illuminate a material being examined and the detectors 410 could measure light from the material being examined at any suitable geometry. During illumination, one or multiple light emitting diodes 402 can be turned on at the same time. In particular embodiments, the light emitting diodes 402 could be pulsed randomly in a cycle and all have constant illumination power. In other particular embodiments, the light emitting diodes 402 could be pulsed randomly in a cycle and have varying illumination powers.

Although FIGS. 4A through 4D illustrate another example of a mechanism for measuring ultraviolet-activated materials in a paper-making process, various changes may be made to FIGS. 4A through 4D. For example, the fluorescence sensor could be used in any other configuration and is not limited to use with just samples, tanks, and pipes. Also, the fluorescence sensor could include any number of light emitting diodes, detectors, controllers, optics, or any other or additional components. In addition, the functional division shown in FIGS. 4A through 4D is for illustration only. Various components in each figure could be combined, subdivided, or omitted and additional components could be added according to particular needs.

In some embodiments, the various detectors in the above-described sensors (such as detectors 206 and 410) can be calibrated to ensure proper operation of the sensors. This may allow, for example, the controller to determine a baseline for measurements made by the detectors. The calibration could occur in any suitable manner, such as by using a calibration tile. The calibration tile could include different areas with known fluorescences. The calibration tile could be illuminated using one or more light emitting diodes or other illumination sources, and measurements of the calibration tile could be taken using the detectors. In this way, the controller can determine how the detectors operate given specific illumination of a surface with known fluorescences.

The calibration could involve any other or additional actions. For example, during calibration, light from the light emitting diodes or other illumination sources can be sampled. This can be done, for instance, by directly measuring the irradiance of at least part of the light to determine its absolute energy. This could also include measuring the irradiance of at least part of the light and using a white standard to normalize the measurements. This could further include diverting at least part of the light and using one or more specific fluorescent standards to normalize measurements of the light with known fluorescent emission properties.

One specific use of a calibration tile is shown in FIG. 4C. Here, a configuration tile 440 resides in and can be moved back and forth within the pipe 432. This may allow, for example, the calibration tile 440 to be moved into the window 434 for calibration of the sensor arrangement and then moved out of the window 434 for measurement of stock or other material in the pipe 432. However, it may be noted that the calibration tile 440 could be used in any other suitable manner. For instance, the calibration tile 440 could reside outside of the pipe 432 and be manually or automatically placed above the window 434. The calibration tile 440 could also be used in any of the other embodiments shown in FIGS. 2 through 4D.

The various sensors 184-193 in the system 100 (however implemented) can be used in any suitable manner to control the operation of the system 100. For example, the sensor 187 can be used to measure the amount of fluorescent material entering the system 100 via the broke chest 158. This determined quantity can be used as a feed-forward control input for controlling the amount of fluorescent whitening agents added at the pump 170. As another example, the sensor 191 can be used to measure the amount of fluorescent material from the white water chest 174. This value can be used to adjust the absorption of fluorescent molecules into stock or paper by, for instance, adjusting the use of fixatives or other chemicals in the stock provided to the headbox 112. As a third example, measurements from the various sensors 184-193 could be used to control the amounts and ratios of various fluorescent fibers, pigments, particles, or other materials used in forming the sheet 108.

The various sensors 184-193 in the system 100 could also be used to control the spatial distribution of ultraviolet-activated materials, such as fluorescent fibers or pigments. For example, measurements from the sensors 188-190 could be used to determine how well the fluorescent fibers or pigments are mixed with the pulp or stock and can be used to adjust the operations of the blend chest 152 or the machine chest 168. As particular examples, the measurements could be used to control mixing conditions in the blend chest 152, such as to dilute a fiber or pigment slurry to a greater or lesser amount. The various sensors could also be used to adjust the dosage ratios in terms of the mean number of fibers or the mean amount of pigment distributed per unit area of the sheet 108.

The measurements from the various sensors 184-193 could be used in any other or additional manner in the system 100. More specifically, the measurements from the various sensors 184-193 could be used to control any other or additional aspects of the paper product being produced. The measurements from the various sensors 184-193 could also be used to adjust any other or additional operations performed in the system 100.

Figure 5:
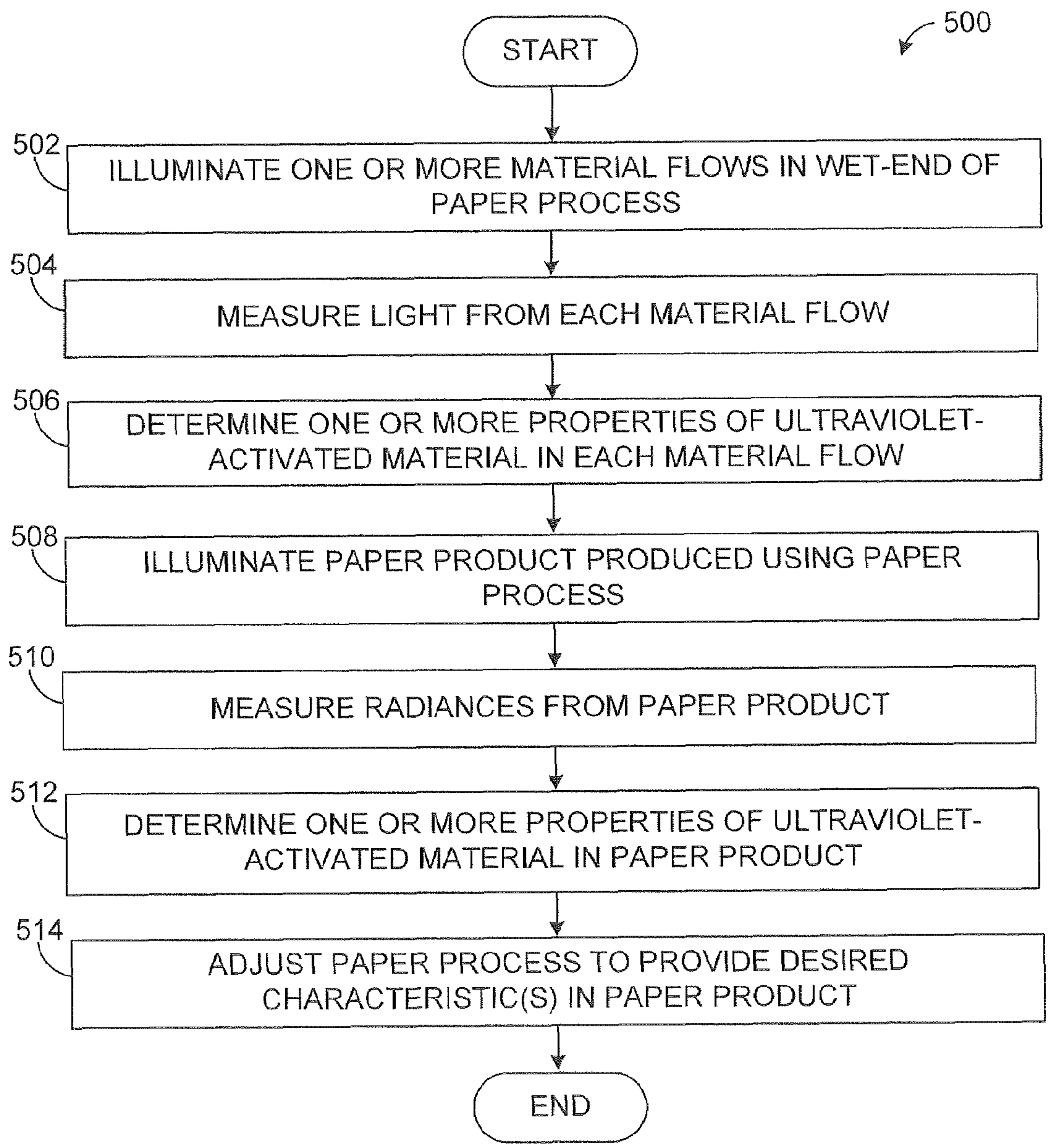
FIG. 5 illustrates an example method for controlling ultra-violet-activated materials in a paper-making process according to this disclosure.

FIG. 5 illustrates an example method 500 for controlling ultraviolet-activated materials in a paper-making process according to this disclosure. The embodiment of the method 500 shown in FIG. 5 is for illustration only. Other embodiments of the method 500 could be used without departing from the scope of this disclosure.

One or more material flows are illuminated in the wet-end of a paper process at step 502. This could include, for example, illuminating material in a tank or pipe using one or more light emitting diodes. The material could be illuminated using at least one ultraviolet wavelength band, which could cause fluorescence of any ultraviolet-activated materials in the flows. Light from each of the material flows is measured at step 504. This could include, for example, measuring the intensity of light reflected from or transmitted through the material flows. The light could be measured over a wide spectral band or in narrow wavelength bands (such as those bands associated with fluorescent emissions). One or more properties of ultraviolet-activated materials in each of the material flows are determined using the measurements at step 506. This could include, for example, determining a quantity of fluorescent materials in each of the material flows.

A paper product produced using the paper process is illuminated at step 508. This could include, for example, illuminating a paper sheet 108 using one or more light emitting diodes. The sheet could be illuminated using at least one ultraviolet wavelength band, which could cause fluorescence of any ultraviolet-activated materials in the sheet. Light from the sheet is measured at step 510. This could include, for example, measuring the intensity of light reflected from or transmitted through the sheet 108. The light could be measured over a wide spectral band or in narrow wavelength bands (such as those bands associated with fluorescent emissions). One or more properties of ultraviolet-activated materials in the sheet are determined using the measurements at step 512. This could include, for example, determining a spatial or average quantity of fluorescent materials in a unit area of the sheet 108.

The paper process is adjusted using the measurements at step 514. This could include, for example, adjusting the amount of broke material used from the broke chest 158. This could also include adjusting the amount of material provided by the sources 160-164 to the blend chest 152. This could further include adjusting the dyes, pigments, fluorescent whitening agents, and other materials added to the stock in the wet-end of the system 100. Any other or additional adjustments could be made to the system 100 based on the measurements.

Although FIG. 5 illustrates one example of a method 500 for controlling ultraviolet-activated materials in a paper-making process, various changes may be made to FIG. 5. For example, while shown as a series of steps, various steps in FIG. 5 could overlap, occur in parallel, occur in a different order, or occur multiple times. Also, only measurements of the material flow(s) or only measurements of the final paper product could be used, so steps 502-506 or steps 508-512 could be omitted.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:

illuminating a mixture of materials in a wet-end of a paper process, the mixture comprising an ultraviolet-activated material;

measuring light from the mixture; and determining a property of the ultraviolet-activated material based on the measured light from the mixture, wherein the property of the ultraviolet-activated material comprises a quantity of the ultraviolet-activated material in the mixture of materials.

2. The method of claim 1, wherein:

illuminating the mixture comprises illuminating the mixture using light in an excitation band associated with the ultraviolet-activated material; and measuring the light from the mixture comprises measuring light in an emission band associated with the ultraviolet-activated material.

3. The method of claim 1, wherein the quantity of the ultraviolet-activated material in the mixture of materials comprises a quantity of fluorescent material in recycled material used to form stock for a paper machine.

4. The method of claim 1, wherein the quantity of the ultraviolet-activated material in the mixture of materials comprises a quantity of fluorescent material in stock provided to a headbox in the paper process.

5. The method of claim 1, further comprising:

adjusting an operation in the wet-end of the paper process based on the determined property of the ultraviolet-activated material.

6. The method of claim 5, wherein adjusting the operation in the wet-end of the paper process comprises adjusting an amount of one or more materials used to form stock provided to a headbox in the paper process.

7. The method of claim 6, wherein the one or more materials used to form the stock comprise at least one of: a fluorescent whitening agent, a fixative, a fluorescent fiber, a fluorescent pigment, a fluorescent particle, a fluorescent highlight, a fluorescent planchette, and a fluorescent quencher.

8. The method of claim 1, further comprising:

illuminating a paper product produced using the paper process, the paper product comprising the ultraviolet-activated material;

measuring second light from the paper product;

determining a property of the ultraviolet-activated material in the paper product based on the measured second light from the paper product; and adjusting the operation in the wet-end of the paper process based on the determined property of the ultraviolet-activated material in the mixture and the determined property of the ultraviolet-activated material in the paper product.

9. The method of claim 8, wherein determining the property of the ultraviolet-activated material in the paper product comprises determining at least one of: a spatial distribution and an average distribution in the paper product of a fluorescent material or of a material whose light absorption or light scattering properties are modified under ultraviolet illumination.

10. The method of claim 9, wherein adjusting the operation in the wet-end of the paper process comprises at least one of:

adjusting a mixing condition in a blend chest in the wet-end; and adjusting a slurry provided to the blend chest.

11. An apparatus comprising:

at least one light emitting diode configured to illuminate a mixture of materials in a wet-end of a paper process using first light, the mixture comprising an ultraviolet-activated material;

at least one detector configured to measure second light from the mixture, the second light based on the first light; and at least one controller configured to determine a property of the ultraviolet-activated material based on the measured second light, wherein the property of the ultraviolet-activated material comprises a quantity of the ultraviolet-activated material in the mixture of materials.

12. The apparatus of claim 11, wherein:

the first light comprises light in an excitation band associated with the ultraviolet-activated material; and the second light comprises light in an emission band associated with the ultraviolet-activated material.

13. The apparatus of claim 11, wherein the quantity of the ultraviolet-activated material in the mixture of materials comprises a quantity of fluorescent material in recycled material used to form stock for a paper machine.

14. The apparatus of claim 11, wherein the quantity of the ultraviolet-activated material in the mixture of materials comprises a quantity of fluorescent material in stock provided to a headbox in the paper process.

15. The apparatus of claim 11, wherein the at least one controller is further configured to adjust an operation in the wet-end of the paper process based on the determined property of the ultraviolet-activated material.

16. The apparatus of claim 15, wherein the at least one controller is configured to adjust an amount of one or more materials used to form stock provided to a headbox in the paper process.

17. An apparatus comprising:

at least one light emitting diode configured to illuminate a mixture of materials in a wet-end of a paper process using first light, the mixture comprising an ultraviolet-activated material;

at least one detector configured to measure second light from the mixture, the second light based on the first light;

at least one controller configured to determine a property of the ultraviolet-activated material based on the measured second light;

a filter configured to filter the second light into at least three spectral bands, wherein different regions of the filter are configured to pass different spectral bands;

wherein the at least one detector is configured to measure the second light in the different spectral bands.

18. The apparatus of claim 17, wherein the property of the ultraviolet-activated material comprises a quantity of fluorescent material in the mixture of materials.

19. A method comprising:

illuminating a paper product produced using a paper process, the paper product comprising an ultraviolet-activated material;

measuring light from the paper product;

determining a property of the ultraviolet-activated material in the paper product based on the measured light from the paper product; and adjusting an operation in a wet-end of the paper process based on the determined property of the ultraviolet-activated material in the paper product, wherein adjusting the operation in the wet-end of the paper process comprises adjusting a composition of a mixture of materials used in the wet-end of the paper process to produce the paper product.

20. The method of claim 19, wherein determining the property of the ultraviolet-activated material in the paper product comprises determining at least one of: a spatial distribution and an average distribution in the paper product of a fluorescent material or of a material whose light absorption or light scattering properties are modified under ultraviolet illumination.

21. The method of claim 19, wherein adjusting the composition of the mixture of materials in the wet-end of the paper process comprises adjusting at least one of: a mixing condition in a blend chest in the wet-end and a slurry provided to the blend chest.

* * * * *